(12) United States Patent
Lee

(10) Patent No.: US 10,967,177 B2
(45) Date of Patent: Apr. 6, 2021

(54) METHOD AND STIMULATION SYSTEM FOR STIMULATING A HUMAN LEG

(71) Applicant: Stichting IMEC Nederland, Eindhoven (NL)

(72) Inventor: Seulki Lee, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 720 days.

(21) Appl. No.: 15/380,413

(22) Filed: Dec. 15, 2016

(65) Prior Publication Data

US 2017/0173325 A1 Jun. 22, 2017

(30) Foreign Application Priority Data

Dec. 22, 2015 (EP) ..................................... 15202057

(51) Int. Cl.
*A61N 1/36* (2006.01)
*A61N 1/04* (2006.01)
*A61H 23/00* (2006.01)

(52) U.S. Cl.
CPC .......... *A61N 1/36003* (2013.01); *A61H 23/00* (2013.01); *A61N 1/0456* (2013.01);
(Continued)

(58) Field of Classification Search
CPC .......... A61H 2205/106; A61H 2205/12; A61H 2230/085; A61H 2230/65; A61H 23/00; A61N 1/0456; A61N 1/0476; A61N 1/0484; A61N 1/36003; A61N 1/36014; A61N 1/36139
(Continued)

(56) References Cited

U.S. PATENT DOCUMENTS 6,282,448 B1  8/2001 Katz et al.
8,738,143 B2  5/2014 Tucker et al.
(Continued)

OTHER PUBLICATIONS

European Search Report, European Patent Application No. 15202057. 4, dated Jun. 8, 2016, 7 pages.
(Continued)

*Primary Examiner* — Niketa I Patel
*Assistant Examiner* — Vynn V Huh
(74) *Attorney, Agent, or Firm* — McDonnell Boehnen Hulbert & Berghoff LLP

(57) ABSTRACT

A method for stimulating a human leg, a stimulation system, and a garment including the stimulation system are disclosed. The method comprises: measuring, by a measuring unit, an electrical characteristic indicative of a physiological condition in a portion of the leg via a subset of skin electrodes comprised in a plurality of skin electrodes integrated in a leg part of a garment arranged to be worn about at least a part of the human leg; determining, by evaluating the measured electrical characteristic, if the portion of the leg is to be stimulated; and if it is determined that the portion is to be stimulated, applying a stimulation via a subset of stimulation units, comprised in a plurality of stimulation units being arranged in the leg part of the garment, such that the portion of the leg is stimulated. A stimulation system and a garment comprising such as stimulation system are also disclosed.

17 Claims, 3 Drawing Sheets

(52) U.S. Cl.
CPC ......... *A61N 1/0476* (2013.01); *A61N 1/0484* (2013.01); *A61N 1/36031* (2017.08); *A61H 2205/106* (2013.01); *A61H 2205/12* (2013.01); *A61H 2230/085* (2013.01); *A61H 2230/65* (2013.01); *A61N 1/36139* (2013.01)

(58) Field of Classification Search
USPC .......................................................... 607/62
See application file for complete search history.

(56) References Cited

U.S. PATENT DOCUMENTS

| | | | |
|---|---|---|---|
| 2004/0019369 A1* | 1/2004 | Duncan .............. | A61N 1/36003 607/46 |
| 2006/0085047 A1 | 4/2006 | Unsworth et al. | |
| 2009/0118790 A1 | 5/2009 | Van Herk | |
| 2010/0004715 A1* | 1/2010 | Fahey ................. | A61N 1/36003 607/48 |
| 2013/0085420 A1 | 4/2013 | Feinstein | |
| 2013/0123568 A1 | 5/2013 | Hamilton et al. | |
| 2014/0046423 A1* | 2/2014 | Rajguru ............... | A61N 1/0456 607/144 |

OTHER PUBLICATIONS

Hanus, S. et al., "Smart Textiles for Medical Applications", The Institute for Special Textiles and Flexible Materials, TITV, DIN ISO 16016, Jun. 11/12, 2012, 43 pages.

* cited by examiner

METHOD AND STIMULATION SYSTEM FOR STIMULATING A HUMAN LEG

CROSS-REFERENCE

This application claims priority from EP 15202057.4, filed on Dec. 22, 2015, which is incorporated by reference in its entirety.

TECHNICAL FIELD

The disclosure relates to a method and a stimulation system for stimulating a human leg, as well as a garment comprising such a stimulation system. The method and stimulation system are suitable for implementation in a garment adapted to be worn about at least a part of a human leg.

BACKGROUND OF THE DISCLOSURE

People today tend live an increasingly sedentary life both when working and during leisure time. There is for example a tendency to spend more time in front of electronic devices. Time spent on traveling, for example by commuting or being on vacation, also tends to increase.

One drawback with the sedentary lifestyle is that the human body is not adapted to long periods of immobility. One symptom that may arise in the body during longtime immobility is the formation of blood clots in leg veins, which is known as deep vein thrombosis. This state is potentially serious and can even have fatal consequences. Deep vein thrombosis is especially common in connection to long airplane flights, and has therefore also been given the alternative name economy class syndrome.

In order to avoid such symptoms, moving around and maintaining a good hydration level are recommended. It is also beneficial to apply stimulation to the legs. The stimulation may be in the form of electrical stimulation or manually performed (mechanical) massage. A purpose of the stimulation is to reduce fluid accumulated in the leg. Stimulation of the leg may be beneficial for other purposes as well such as for relieving varicose veins.

Patent application US20060085047 relates to a system for automatic electrical muscle stimulation for prevention of deep vein thrombosis. The disclosed system comprises electrodes placed on for example a sock. Stimulation of the type neuromuscular electrical stimulation (NMES) is applied.

There is, however, a need for improvement in view of efficiency of systems and methods providing stimulation to a leg. There is also a need for improving the comfort for the user who is exposed to the stimulation.

SUMMARY OF THE DISCLOSURE

It is a general object of the present disclosure to provide a method and a system for stimulating a human leg. Specifically, an object of the disclosure is to provide an efficient method which improves the comfort for the user in view of known solutions.

According to a first aspect, a method for stimulating a human leg is provided. The method comprises: measuring, by a measuring unit, an electrical characteristic indicative of a physiological condition in a portion of the leg via a subset of skin electrodes comprised in a plurality of skin electrodes integrated in a leg part of a garment adapted to be worn about at least a part of the human leg; determining, by evaluating the measured electrical characteristic, if the portion of the leg is to be stimulated; and if it is determined that the portion is to be stimulated, applying a stimulation via a subset of stimulation units, comprised in a plurality of stimulation units being arranged in the leg part of the garment, such that the portion of the leg is stimulated.

The term subset can be interpreted as strict subset, meaning that the subset can be formed by one or more components, but not all, of a plurality of components.

The method implements the concept of measuring selected portions of the leg via skin electrodes integrated into a garment and applying stimulation to portions of the leg which are determined to need stimulation. The method thus enables portions of a human leg which need stimulation to be selectively stimulated. The method enables a more efficient and comfortable stimulation of the leg. Specifically, the method is efficient in that the stimulation can be adapted to stimulate a specific portion, which is determined to need stimulation, instead of stimulating the whole part of the leg which is available for stimulation. By portion of the leg is thus meant a sub-part of the leg that is covered by the garment when worn.

Since the method can be implemented by components provided in a garment, a mobile power source such as a battery may be integrated in the garment. A power-efficient method, such as the one disclosed herein, can provide the advantage of utilizing the limited battery resources in an efficient manner.

The garment may be a textile article. The garment may be made of a flexible material. The garment may be adapted to provide a tight fit about the leg part when the garment is worn. The garment can form part of a stocking, tights or a sock. These shapes can be examples of practical forms of the garments which are easy to adapt to from a user-perspective.

In one embodiment, the subset of skin electrodes forms a first subset of skin electrodes and the method further comprises: measuring, by the measuring unit, an electrical characteristic indicative of a physiological condition in a second portion of the leg via a second subset of skin electrodes comprised in the plurality of skin electrodes, determining, by evaluating the measured electrical characteristic, if the second portion of the leg is to be stimulated; and if it is determined that the second portion is to be stimulated, applying a stimulation via a second subset of stimulation units, comprised in the plurality of stimulation units, such that the second portion of the leg is stimulated.

In this embodiment, two different leg portions can be measured and independently and selectively stimulated by respective subsets of stimulation units. The leg portions may be separate from each other or may overlap each other to some extent.

The physiological condition may be fatigue, stress, edema, or a combination thereof.

In one embodiment, the measurement includes measuring impedance, such as body impedance, in the portion of the leg via the subset of skin electrodes.

The impedance in a leg portion can vary with some physiological conditions of the leg portion and may hence form a relevant measurement on which the decision of applying a stimulation or not may be based. In one embodiment, the subset of skin electrodes may include at least two pairs of skin electrodes wherein the impedance of the portion of the leg may be measured via the at least two pairs of skin electrodes.

In one embodiment, the measurement can include measuring an electrical muscle potential in the portion of the leg via the subset of skin electrodes.

The electrical muscle potential in a leg portion can vary with some physiological conditions of the leg portion and may hence form a relevant measurement on which the decision of applying a stimulation or not may be based. In particular, by measuring an electrical muscle potential, an electromyogram may be recorded for the leg portion.

In one embodiment, the method can include measuring, by the measuring unit, impedance in the portion of the leg via the subset of skin electrodes and an electrical muscle potential in the portion of the leg via the subset of skin electrodes. The determination of whether the portion of the leg is to be stimulated may thereby be based on an evaluation of the measured impedance and of the measured electrical muscle potential.

In one embodiment, the method may further comprise: if stimulation is applied to the portion, measuring, by the measuring unit, a further electrical characteristic indicative of the physiological condition in the portion of the leg via the subset of skin electrodes; determining, by evaluating the measured further electrical characteristic, if the stimulation of the leg is to be adjusted; and if it is determined that the stimulation is to be adjusted, configuring the subset of stimulation units, such that the applied stimulation of the leg is adjusted.

This embodiment can provide a feedback loop in which stimulation applied to a leg portion may be adjusted depending on how the physiological condition of the leg portion, that is stimulated, changes.

In one embodiment, the subset of stimulation units can be configured by altering at least one of the stimulation amplitude, the stimulation frequency and the duration of the stimulation.

In one embodiment, the subset of stimulation units can be configured such that the stimulation of the leg is terminated. The stimulation may hence be adjusted to be terminated if it is determined that no more stimulation is needed.

In one embodiment, the method further comprises: if the applied stimulation is terminated, measuring, by the measuring unit, an electrical characteristic indicative of a physiological condition in a second portion of the leg via a second subset of skin electrodes comprised in the plurality of skin electrodes, determining, by evaluating the measured electrical characteristic, if the second portion of the leg is to be stimulated; and if it is determined that the second portion is to be stimulated, applying a stimulation via a second subset of stimulation units, comprised in the plurality of stimulation units, such that the second portion of the leg is stimulated.

In other words, the method may comprise measuring and applying stimulation, on a condition that it is determined to be needed, on a first portion of the leg, until it is determined that stimulation is not needed whereby the stimulation is terminated. A second portion of the leg is then measured and stimulation is applied to the second portion if it is determined that stimulation is needed. This step-wise measuring and stimulation (with adjustment) of different portions of the leg may be performed on further portions of the leg (a third portion, a fourth portion, etc.).

In one embodiment, the method further comprises: measuring, by a motion sensing unit arranged in the garment, a movement of the leg; wherein also the measured movement is evaluated for determining if the portion of the leg is to be stimulated.

By this embodiment, the activity level of the user may be taken into account when determining whether to apply stimulation or not. In one embodiment, the motion sensing unit can be provided in a part of the garment that is adapted to be worn about at least a part of the foot. Thus, also walking intensity and/or number of taken steps may be measured. These measurements may be taken into account when determining whether to apply stimulation or not.

According to a second aspect, a stimulation system for integration in a garment adapted to be worn about at least a part of a human leg is provided. The stimulation system comprises: a plurality of skin electrodes arranged to be integrated in a leg part of the garment; a measuring unit connected to the plurality of skin electrodes, the measuring unit being arranged to measure, via a subset of skin electrodes comprised in the plurality of skin electrodes, an electrical characteristic indicative of a physiological condition in a portion of a human leg when the garment is worn; a plurality of stimulation units being arranged in the leg part of the garment; a controller being configured to determine if the portion of the leg is to be stimulated by evaluating the measured electrical characteristic, and configured to, if it is determined that the leg is to be stimulated, apply a stimulation via a subset of stimulation units, comprised in the plurality of stimulation units, such that the portion of the leg is stimulated.

The above features and advantages disclosed in connection to the first aspect apply also to this second aspect. To avoid undue repetition, reference is made to the above.

In one embodiment, the subset of stimulation units can comprise an electrical stimulator or a mechanical stimulator.

In one embodiment, the subset of stimulation units can comprise both an electrical stimulator and a mechanical stimulator. Both electrical stimulation and mechanical stimulation may thus be applied, which may reduce fluid accumulated in the leg in an efficient manner.

In one embodiment, the subset of stimulation units can comprise an electrical stimulator configured to apply transcutaneous electrical nerve stimulation, TENS.

In one embodiment, the subset of skin electrodes can comprise at least one pair of skin electrodes.

A pair of skin electrodes can enable measurement of an electrical characteristic such as impedance in the leg portion or an electrical muscle potential in the leg portion. In one embodiment, the subset of skin electrodes can include at least two pairs of associated skin electrodes wherein the impedance or the electrical muscle potential of the portion of the leg may be measured via the two pairs of skin electrodes.

In one embodiment, the plurality of stimulation units can comprise electronic stimulators formed by one or more of the plurality of skin electrodes.

Hence, a same skin electrode may be provided with a double function of serving as a measurement electrode and as a stimulation electrode. This embodiment can enable the total number of electrodes to be reduced without impairment of the functionality of the system.

In one embodiment, the stimulation system may further comprise a motion sensing unit arranged to be integrated in the garment and arranged to measure a movement of the leg, wherein the controller can be arranged to evaluate also the measured movement for determining if the portion of the leg is to be stimulated. Reference is made to the above disclosure of functions and advantages of the motion sensing unit.

According to a third aspect, a garment adapted to be worn about at least a part of a human leg is provided. The garment can comprise a system according to the above disclosed second aspect.

Generally, all terms used in the claims are to be interpreted according to their ordinary meaning in the technical field, unless explicitly defined otherwise herein. All references to "a/an/the [element, device, component, means, step, etc.]" are to be interpreted openly as referring to at least one instance of the element, device, component, means, step, etc., unless explicitly stated otherwise. The steps of any method disclosed herein do not have to be performed in the exact order disclosed, unless explicitly stated.

BRIEF DESCRIPTION OF DRAWINGS

The above disclosed and other aspects of the present disclosure will now be described in more detail, with reference to the appended drawings showing embodiments of the disclosure.

Note that figures are not to scale for purposes of clarity.

DETAILED DESCRIPTION OF THE DISCLOSURE

The present disclosure will now be described more fully with reference to the accompanying drawings, in which representative embodiments of the disclosure are shown. The disclosure may however be embodied in many different forms and should not be construed as limited to the embodiments set forth herein.

Figure 1:
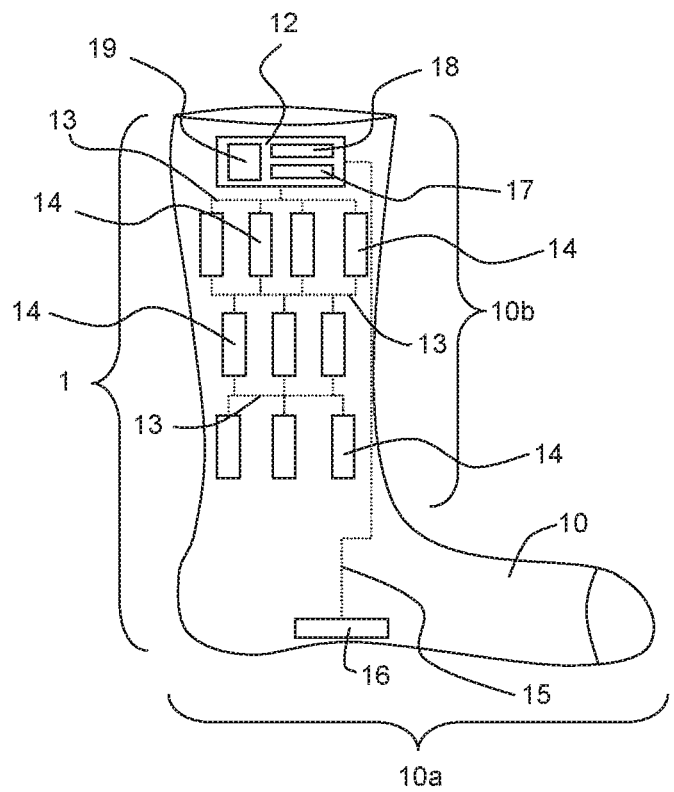
FIG. 1 illustrates a sock in which a stimulation system is integrated.

A garment in the form of a sock 10 having a stimulation system 1 integrated therein is illustrated in FIG. 1. The stimulation system 1 can be disclosed as being integrated in the sock 10 which forms the garment adapted to be worn about at least a part of a human leg. It is however appreciated that other types of garments, such as a stocking, tights or sleeves, are feasible.

The sock 10 can be divided into a foot part 10a and a leg part 10b. The form of the sock 10 is only for illustrative purposes. The sock 10 may be shaped differently such as having a longer or shorter leg part or be designed without a portion covering the toes of a wearer's foot. It is moreover not necessary that the sock 10 is formed by a closed tube of textile, but could instead be formed by a textile that is wrapped around a part of the leg and the foot such that a sock-like shape is achieved.

The stimulation system 1 can comprise a plurality of connected components which can be integrated in the textile of the sock 10. The integration may be achieved in various conventional ways. Non-limiting examples of how components may be integrated in the textile are by use of textile connectors such as metal buttons or clips, or by use of electronic connectors such as a connector for a SD (Secure Digital) card a micro-SD card. Non-limiting examples of how interconnections between the components may be achieved are by use of conductive yarns, by printing conductive paste on the textile, or by laminating conductive paths on the textile.

The stimulation system 1 can comprise a central unit 12, a plurality of array units 14 and a motion sensing unit 16. The central unit 12 can be connected to each of the array units 14 by interconnections 13 and to the motion sensing unit 16 by an interconnection 15. The illustration of the interconnections 13 are simplified in this figure for purposes of clarity. However, the central unit 12 may be connected to each of the array units 14 by a respective single interconnection.

The central unit 12 can comprise a measuring unit 17, a controller 18 and a battery 19. These components need not be located in a single unit. For example, the battery 19 may be located in another portion of the sock, such as in the foot part 10a or in a lower portion of the leg part 10b.

The stimulation system 1 can further comprise a plurality of skin electrodes and a plurality of stimulation units which can be comprised in the array units 14. Each array unit 14 can comprise one or more skin electrodes and/or one or more stimulation units. The configuration of the array units 14 may thus differ between different embodiments. In one embodiment, each array unit 14 can comprise one or more skin electrodes and one or more stimulation units.

The measuring unit 17 can be arranged to perform measurements via a subset of skin electrodes of the plurality of skin electrodes. The skin electrodes can be arranged to sense an electrical characteristic, for example an electrical biosignal such as a body impedance which may be performed by providing electrical current via two skin electrodes and measuring a resulting voltage via two other skin electrodes. The skin electrodes can be arranged to make galvanic contact with a respective part of the human leg when the sock 10 is arranged thereon.

Each skin electrode may include a separate conductive portion. Each conductive portion may include a conductive material such as stainless steel, copper, aluminum, gold, silver, silver-chloride or carbon, to name a few. The conductive material may be arranged as a thin layer on the inner surface of the sock textile. According to further options a conductive portion may be formed by a patch of conductive ink deposited on the surface of the sock textile, or by a conductive yarn incorporated into the textile (i.e. interwoven in a woven material).

It is noted that the measuring unit 17 may be composed of a plurality of elements for performing measurements via the skin electrodes. The illustrated measuring unit 17 could be seen as representing one or more measuring circuitries which together can provide the function of measuring via (a subset of) the skin electrodes. The measuring circuitry/circuitries could be positioned at different locations in the sock 10 and thus need not be located in the central unit 12.

Each stimulation unit can be arranged to stimulate a part of the human leg when the sock 10 is worn. The stimulation unit may comprise an electrical stimulator, a mechanical stimulator or a combination thereof. A non-limiting example of an electrical stimulator which may be used is a TENS stimulator, i.e. an electrical stimulator configured to apply transcutaneous electrical nerve stimulation (TENS) to the leg portion. TENS may be applied by a subset of stimulation units comprising two or more stimulation units comprising electrodes.

The stimulation system can thus be adapted to perform measurement and apply stimulation to portions of the leg. The portion of the leg that is measured on and conditionally stimulated can depend on the configuration of the stimulation system 1. A subset of skin electrodes comprised in the plurality of skin electrodes may be chosen for measuring on a specific portion of the leg. By portion, that is measured on and possible stimulated, can mean a sub-part of the covered leg. Each array unit 14 may be said to cover a portion of the leg. Two or more array units 14 may alternatively be said to together cover a portion of the leg.

Measurements may be performed by skin electrodes within a single array unit 14 or arranged in multiple array units 14. Stimulation may be performed by stimulation units within a single array unit 14 or arranged in multiple array units 14. In one embodiment, measurements and possible stimulation can be performed by skin electrodes and stimulation units within a single array unit 14.

The subset of stimulation units can be selected so as to stimulate the portion of the leg that is determined to need stimulation based on the measurements via the subset of skin electrodes. The subset of stimulation units need not be located in the same array elements 14 as the skin electrodes. It is noted that multiple configurations of subsets of skin electrodes and subsets of stimulation units are possible in order to measure on or apply stimulation to a leg portion.

The motion sensing unit 16 can comprise a conventional sensor for sensing motion, such as an accelerometer or an IMU (inertial measurement unit). The motion sensing unit 16 can thus be able to measure movement of the sock 10 and thereby of the human leg when the sock 10 is worn. The motion sensing unit 16 can be arranged to provide measurement value(s) to the controller 18 of the central unit 12, which measurement value(s) corresponds to measured movement.

In one embodiment, a stimulation unit may comprise an electronic stimulator which may be formed by one or more of the skin electrodes via which the corresponding measurement has been performed. In other words, a skin electrode may form a measuring electrode for measuring and also a stimulation electrode for applying stimulation.

In one embodiment, the array units 14 can be arranged around the whole leg portion 10*b* of the sock in order to provide positions for measurement/stimulation in various parts of the human leg.

Figure 2:
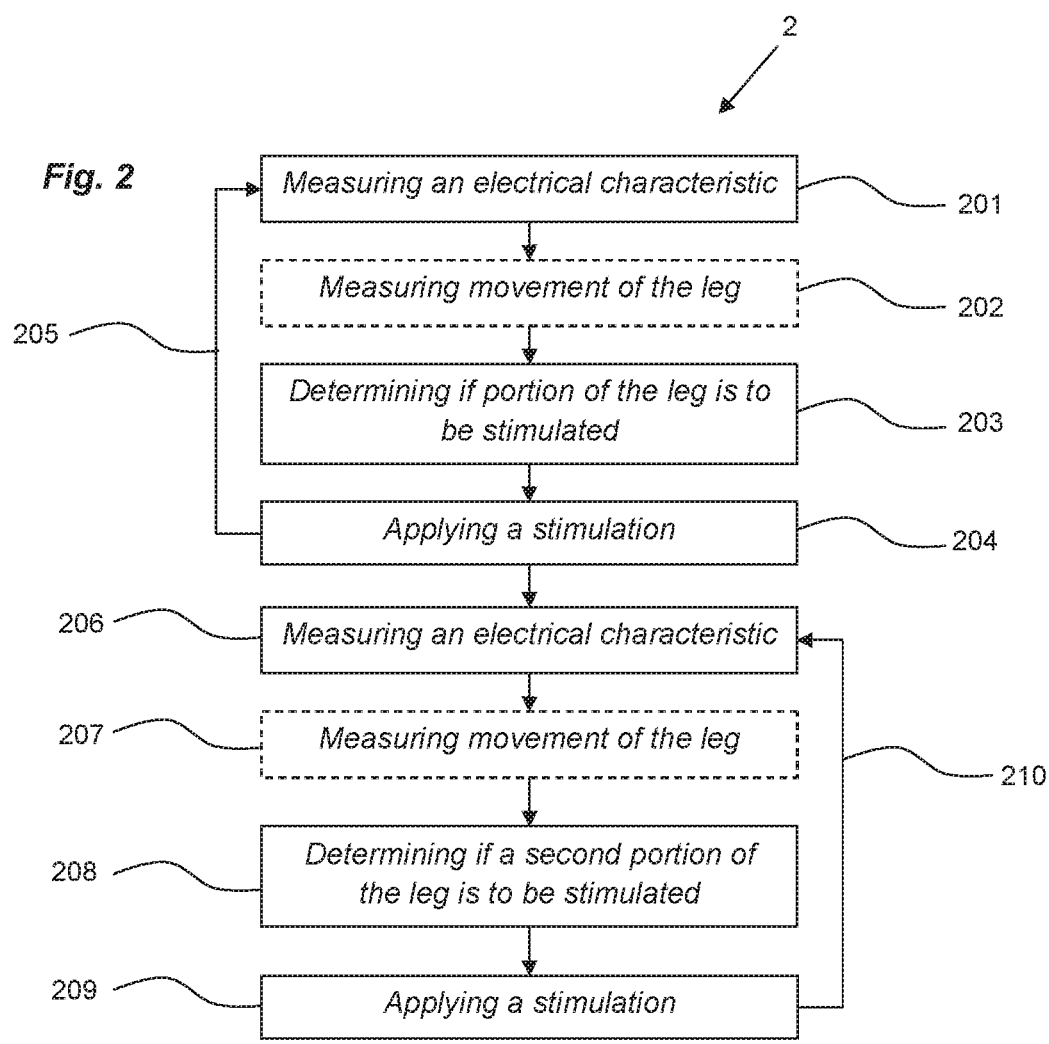
FIG. 2 illustrates a method for stimulating a human leg.

The stimulation system 1 can implement a method for stimulating a human leg when the sock 10 is arranged thereon. FIG. 2 illustrates an embodiment of a method 2 which may be performed by the stimulation system 1 of FIG. 1. The method 2 will now be disclosed in detail with reference to also FIG. 1.

The method 2 can comprise measuring 201 an electrical characteristic. The electrical characteristic can be measured by the measuring unit 17 via a subset of skin electrodes comprised in the plurality of skin electrodes. The subset of skin electrodes can be chosen by the controller 18 so as to measure an electrical characteristic indicative of a physiological condition in a specific portion of the leg. In other words, the plurality of skin electrodes may comprise a plurality of subsets which corresponds to measuring on different portions of the leg. It is noted that a single skin electrode in the plurality of skin electrodes may be part of multiple subsets of skin electrodes.

The physiological condition which is to be measured may be for example fatigue, stress, edema, or a combination thereof. A fatigue level may be measured by measuring electrical muscle potential as electrical characteristic. Edema may be measured by measuring impedance as electrical characteristic.

The method 2 can further comprise determining 203 if the portion of the leg, that the measurement 201 corresponds to, is to be stimulated. The determination 203 can comprise evaluating the measured 201 electrical characteristic. The determination 203 and evaluation thereof can be performed by the controller 18. The evaluation may comprise comparing the electrical characteristic with a predetermined threshold. For example, an electrical characteristic indicative of the physiological condition of fatigue may be compared to a predetermined fatigue level threshold. If the electrical characteristic is above the threshold, it may be decided that stimulation of the measured leg portion is needed. The evaluation may alternatively comprise a lookup in a predetermined table in which it is indicated if stimulation is needed or not for different measurement values of the electrical characteristic.

The method may further comprise, if it is determined that stimulation of the leg portion is needed, determining which type of stimulation (e.g. electrical and/or mechanical) that should be applied and with which configuration (e.g. stimulation amplitude, stimulation frequency, duration of the stimulation).

The method 2 can further comprise applying 204 a stimulation on the condition that it is determined 203 that the portion of the leg is to be stimulated. The stimulation can be applied 204 via a subset of stimulation units which can be comprised in one or more of the array units 14. The subset of stimulation units can be chosen so as to stimulate the specific portion of the leg that has been measured on. The plurality of stimulation units may comprise a plurality of subsets which correspond to stimulation of different portions of the leg. It is noted that a single stimulation unit in the plurality of stimulation units may be part of multiple subsets of stimulation units.

In other words, the method 2 can comprise measuring an electrical characteristic indicative of a physiological condition in a first portion of the leg, determining, if the first portion of the leg is to be stimulated and applying stimulation such that the first portion of the leg is stimulated. The method 2 can thereby implement the concept of measuring a selected portion of the leg via skin electrodes integrated into a sock and applying stimulation such that the selected portion of the leg which is determined to need stimulation is stimulated. The method can thus enable portions of a leg, covered by the sock 10, which need stimulation to be selectively stimulated.

The stimulation system 1 may be configured differently in view of the skin electrode and the stimulation units depending on for example which physiological condition that is desired to base the determination of stimulation on or which stimulation method that is desired to achieve. Different embodiments of skin electrode configurations and stimulation unit configurations will now be disclosed.

In one embodiment, the plurality of skin electrodes can be arranged to measure impedance. In other words, the measured electrical characteristic can relate to impedance. The impedance can vary with physiological conditions such as edema. The measured electrical characteristic may thus be indicative of such a physiological condition.

For an impedance measurement, such as a body impedance measurement, the subset of skin electrodes can comprise at least one pair of associated first and second skin electrodes each formed by a bio-impedance sensor.

In one embodiment, two pairs of skin electrodes can be utilized. The impedance measurement may in such an embodiment be conducted by that a small alternating current (AC) is applied by a first electrode in a first pair of skin electrodes and received by a first electrode in a second pair of skin electrodes. A potential drop can be sensed between the second skin electrodes of the first and second pairs of skin electrodes. The impedance can be determined based on the measured potential drop.

In one embodiment, each pair of skin electrodes may be chosen such that the pair of skin electrodes are located with a distance of for example 2-3 cm between each other. In some embodiments, the skin electrodes within a pair may be chosen from the same array unit 14.

This type of measurement may be repeated for different skin electrode configurations within the subset. The result may be measurement values corresponding to a two-dimensional tomogram on which the determination of whether stimulation is to be applied is (partly or fully) based on. The impedance measurement may thus be used to contribute in an electro-impedance tomography (EIT) measurement.

In one embodiment, the plurality of skin electrodes can be arranged to measure an electrical muscle potential. In other words, the measured electrical characteristic can relate to electrical muscle potential. The electrical muscle potential can vary with physiological conditions such as fatigue and muscle contraction. The measured electrical characteristic may thus be indicative of such physiological conditions.

For instance, the subset of skin electrodes can comprise at least one pair of associated first and second skin electrodes designed to measure a potential between them over a surface area of the portion of the leg. In one embodiment, the at least one pair of skin electrodes may be chosen to be located with a distance of for example 2-3 cm between each other. In another embodiment, the skin electrodes within a pair may be chosen from the same array unit 14.

The subset of skin electrodes may further comprise a reference skin electrode via which a reference value for the measurement may be measured.

The electrical muscle potential measurement may result in measurement values corresponding to an electromyogram on which the determination of whether stimulation is to be applied is (partly or fully) based on.

In one embodiment, the measurement 201 may comprise both measurements of impedance and of an electrical muscle potential. The determination of whether stimulation is to be applied or not may comprise evaluation of measurement values from both types of measurements. The determination may thus take the status of multiple physiological conditions in account which may result in a more accurate decision on whether stimulation is to be applied or not, or which type of stimulation that is to be applied.

The method 2 may comprise a step of measuring 202 movement of the leg. The measurement can be performed by the motion sensing unit 16. Non-limiting parameters that may be measured are movement of the leg, walking intensity, and number of taken steps during predetermined period of time. The measurement values may be taken into account during the evaluation of the measured electrical characteristic for determining if and what kind of stimulation is to be applied. The electrical characteristic may be evaluated differently based on if the leg is moving or not which may be indicated by the measurement values provided by the motion sensing unit. For example, a portion of a non-moving leg (as measured by the motion sensing unit) may be determined to need stimulation whereas the same portion of a moving leg (as measured by the motion sensing unit) may be determined to not need stimulation even if the measured electrical characteristic(s) is the same in both evaluations.

The method 2 can further comprise a repetition 205 of the operations of measuring 201 an electrical characteristic, optionally measuring 202 movement of the leg, determining 203 if stimulation is to be applied, and applying 204 stimulation. When repeated, the operation of measuring 201 can comprise measuring 201 a further electrical characteristic indicative of the physiological condition in the first portion of the leg. The purpose of this measurement can be to determine if the applied stimulation is to be adjusted. In other words, the method 2 may comprise determining, by evaluating the measured further electrical characteristic if the stimulation of the first portion of the leg is to be adjusted. The determination can be made by the controller 18 and can comprise evaluation of the measured further electrical characteristic. If it is determined that the stimulation is to be adjusted, the controller 18 can configure the subset of stimulation units (that is selected to apply stimulation) such that the stimulation of the first portion of the leg is adjusted accordingly. The adjustment may comprise altering a parameter of the stimulation unit, such as stimulation amplitude, stimulation frequent, or set duration of stimulation. The adjustment may alternatively comprise termination of the stimulation based on that it is determined that no more stimulation is needed.

The method 2 may comprise multiple feedback loops as the one indicated by 205.

The method 2 can further comprise measuring 206 an electrical characteristic indicative of a physiological unit in a second portion of the leg. The measurement 206 can be made by the measuring unit 17 and via a second subset of skin electrodes comprised in the plurality of skin electrodes. The method can further comprises determining 208, by the controller 18, if the second portion of the leg is to be stimulated by evaluating the measured electrical characteristic provided by the measurement in operation 206. If it is determined that the second portion is to be stimulated, the method 2 can further comprise applying 209 a stimulation via second subset of stimulation units comprised in the plurality of stimulation units, such that the second portion of the leg is stimulated.

The method 2 may further comprise measuring 207 movement of the leg. This measurement may be taken into account when determining 208 if stimulation is to be applied, as disclosed in detail above in connection to measuring 202 movement of the leg.

Hence, multiple different portions of the leg may be evaluated for stimulation by implementation of the method 2 and by the stimulation system 1. It is noted that even though a portion of the leg is evaluated for stimulation, by measuring and evaluating an electrical characteristic, stimulation need not be applied. On the contrary, stimulation can be applied based on the determination and not by default without any consideration. In other words, the method 2 can provide selective stimulation of different portions of the leg.

Figure 3:
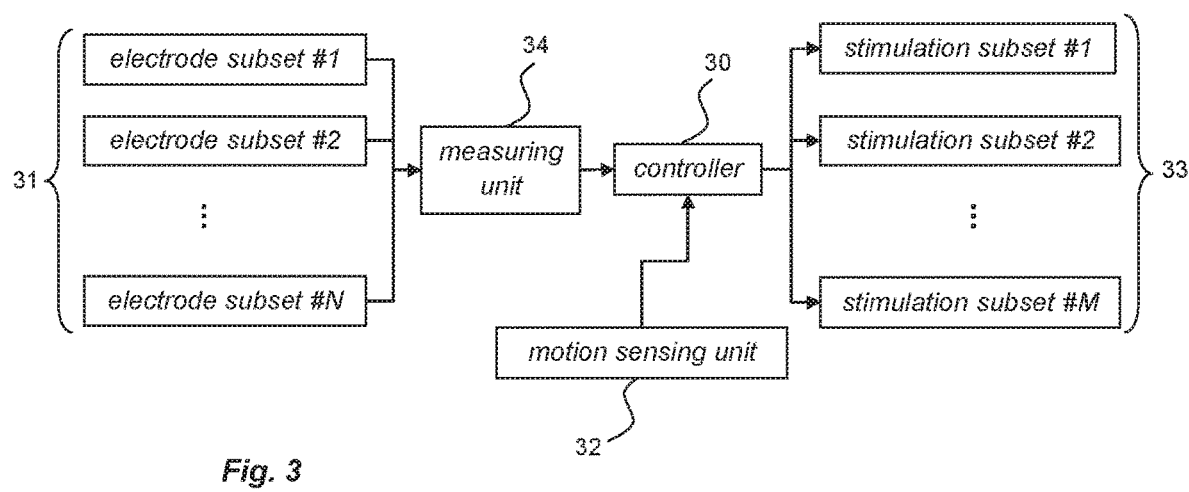
FIG. 3 illustrates an operational structure for a stimulation system.

An operational structure which may be implemented in the stimulation system 1 in FIG. 1 is illustrated in FIG. 3. A controller 30, such as the controller 18 of the stimulation system 1, can form the central operational unit of the structure. The controller 30 can be connected to a measuring unit 34 which in turn can be connected to electrode subsets 31. The controller 30 can be further connected to a motion sensing unit 32 and to stimulation subsets 33.

The number of electrode subsets 31 can be N, i.e. there is a first electrode subset, a second electrode subset, continuing up to an $N^{th}$ electrode subset. The number of stimulation subsets 33 can be M, i.e. there is a first stimulation subset, a second stimulation subset, continuing up to an $M^{th}$ stimulation subset. The electrode subsets 31 can correspond to measuring different portions of the leg. The stimulation subsets 33 can correspond to applying stimulation to different portions of the leg.

The connection between the measuring unit 34 and each of the electrode subsets 31 can each formed by the one or more connections to the one or more skin electrodes which are part of the particular subset (#1, #2, . . . , #N) of skin electrodes in the plurality of skin electrodes, such as the one in the stimulation system 1. A single skin electrode may be part of multiple electrode subsets.

Each of the connections between the controller 30 and each of the stimulation subsets 33 can be formed by the one or more connections to the one or more stimulation units which are part of the particular subset (#1, #2, . . . #M) of stimulation units in the plurality of stimulation units, such as the one in the stimulation system 1. A single stimulation unit may be part of multiple stimulation subsets.

The motion sensing unit 32 can be connected to the controller so as to provide measurement values pertaining to movement of the leg as disclosed above.

A scenario of a selective and stepwise evaluation and stimulation of different portions of the leg will now be disclosed.

The controller 30 can initiate measurement of a physiological condition of a first portion of the leg by requesting and obtaining measured electrical characteristic from the measuring unit 34 as measured via the electrode subset #1. It is noted that the measuring unit 34 may perform measurements (possible continuously) via all skin electrodes in the plurality of skin electrodes but provides only the measurements values from the skin electrodes of the subset of skin electrodes that is requested by the controller 30.

The controller 30 can evaluate, possible with additional measurement values from the motion sensing unit 32, the measured electrical characteristic and can determine if the first portion of the leg is to be stimulated. If so, the controller 30 can initiate application of the stimulation via the stimulation subset #1 which can be arranged to stimulate the first portion of the leg. After a predetermined period of time of stimulation of the first portion of the leg, the controller 30 may terminate the stimulation by instructing the stimulation subset #1 to terminate stimulation. The controller 30 may request and obtain measured further electrical characteristic from the measuring unit 34 which performs the measurement still via the electrode subset #1. The controller 30 may evaluate the further electrical characteristic and determine if the stimulation is to continue and in that case if the stimulation is to be changed and instruct the stimulation subset #1 accordingly. When the controller 30 determines that no more stimulation for the first portion of the leg is needed, the controller 30 can request and obtain measured electrical characteristic from the measuring unit 34 as measured via the electrode subset #2. This measured electrical characteristic can correspond to measurements on a second portion of the leg. The controller 30 can evaluate, determine and possibly instruct on stimulation for the second portion of the leg via the stimulation subset #2 in the same manner as for the first portion of the leg. When measuring and stimulation, if needed, of the $N^{th}$ portion of the leg has been performed and found satisfying, i.e. no more stimulation is needed at the moment, the controller 30 may repeat the process by requesting and obtaining measurement characteristic corresponding to the first portion of the leg. Thus, a selective and stepwise evaluation of different portions of the leg can be achieved.

The person skilled in the art realizes that many modifications and variations are possible within the scope of the appended claims. For example, in the above disclosed scenario it is noted that different parts may be altered or combined to new scenarios. For example, depending on the configuration of the stimulation system, termination of the stimulation may be necessary in order to perform measurements via an electrode subset. For stimulation systems in which it is possible to perform accurate measurements during stimulation, the stimulation need of course not be terminated. As another example, the stepwise stimulation may be performed without multiple measurements of a current portion of the leg. Stimulation of a portion of the leg may be evaluated by the controller 30 and applied during a predetermined period of time if it is determined to be needed for that portion. When the predetermined period of time has lapsed, the controller 30 may move on to the next portion of the leg by requesting and evaluating electrical characteristic as measured on that next portion. This scenario provides a stepwise stimulation of different portions of the leg in which it is assured that all portions of the leg, which are covered by the stimulation system, are stimulated if needed within a certain period of time.

What is claimed:

1. A method for stimulating a human leg, the method comprising:
   measuring, by one or more measuring circuitries, an electrical characteristic indicative of a physiological condition in a first portion of the leg via a first subset of skin electrodes comprised in a plurality of skin electrodes integrated in a leg part of a garment adapted to be worn about at least a part of the human leg;
   determining, by evaluating the measured electrical characteristic from the first portion of the leg, if the first portion of the leg is to be stimulated;
   in response to determining that the first portion is to be stimulated, applying a first stimulation via a first subset of electrical and/or mechanical stimulators, comprised in a plurality of electrical and/or mechanical stimulators, each being connected to a controller by a respective single interconnection and being arranged in the leg part of the garment, such that the first portion of the leg is stimulated;
   in response to applying the first stimulation to the first portion, measuring, by the one or more measuring circuitries, a further electrical characteristic indicative of the physiological condition in the first portion of the leg via the first subset of skin electrodes;
   determining, by evaluating the measured further electrical characteristic, if the first stimulation of the leg is to be terminated;
   in response to determining that the first stimulation is to be terminated, configuring the first subset of electrical and/or mechanical stimulators such that the applied first stimulation of the leg is terminated;
   measuring, by the one or more measuring circuitries, an electrical characteristic indicative of the physiological condition in a second portion of the leg via a second subset of skin electrodes comprised in the plurality of skin electrodes, wherein the second portion of the leg is different than the first portion of the leg, and wherein the second subset of skin electrodes is different than the first subset of skin electrodes;
   determining, by evaluating the measured electrical characteristic from the second portion of the leg, if the second portion of the leg is to be stimulated; and
   in response to determining that the second portion is to be stimulated, applying a second stimulation via a second subset of electrical and/or mechanical stimulators, comprised in the plurality of electrical and/or mechanical stimulators, such that the second portion of the leg is stimulated, wherein the second subset of electrical and/or mechanical stimulators is different than the first subset of electrical and/or mechanical stimulators, and wherein measuring the electrical characteristic indicative of the physiological condition in the second portion of the leg occurs in response to the first stimulation being terminated.

2. The method according to claim 1, wherein the physiological condition is fatigue, stress, edema, or a combination thereof.

3. The method according to claim 1, wherein measuring the electrical characteristic indicative of the physiological condition in the first portion of the leg includes measuring impedance in the first portion of the leg via the first subset of skin electrodes, and wherein measuring the electrical characteristic indicative of the physiological condition in the second portion of the leg includes measuring impedance in the second portion of the leg via the second subset of skin electrodes.

4. The method according to claim 1, wherein measuring the electrical characteristic indicative of the physiological condition in the first portion of the leg includes measuring an electrical muscle potential in the first portion of the leg via the first subset of skin electrodes, and wherein measuring the electrical characteristic indicative of the physiological condition in the second portion of the leg includes measuring an electrical muscle potential in the second portion of the leg via the second subset of skin electrodes.

5. The method according to claim 1, wherein the first subset of electrical and/or mechanical stimulators is configured to alter at least one of stimulation amplitude, stimulation frequency and duration of the stimulation.

6. The method according to claim 1, further comprising:
measuring, by an accelerometer or an inertial measurement unit arranged in the garment, a movement of the leg, wherein also the measured movement is evaluated for determining if the first and second portions of the leg are to be stimulated.

7. The method according to claim 1, wherein the first subset of skin electrodes and the second subset of skin electrodes share at least one skin electrode from the plurality of skin electrodes, and wherein the first subset of electrical and/or mechanical stimulators and the second subset of electrical and/or mechanical stimulators share at least one electrical and/or mechanical stimulator from the plurality of electrical and/or mechanical stimulators.

8. A stimulation system for integration in a garment adapted to be worn about at least a part of a human leg, the stimulation system comprising:
a plurality of skin electrodes arranged to be integrated in a leg part of the garment;
a plurality of electrical and/or mechanical stimulators being arranged in the leg part of the garment; and
a controller being configured to perform operations including:
measuring, by one or more measuring circuitries connected to the plurality of skin electrodes, an electrical characteristic indicative of a physiological condition in a first portion of the leg via a first subset of skin electrodes comprised in the plurality of skin electrodes;
determining, by evaluating the measured electrical characteristic from the first portion of the leg, if the first portion of the leg is to be stimulated;
if it is determined that the first portion is to be stimulated, applying a first stimulation via a first subset of electrical and/or mechanical stimulators, comprised in the plurality of electrical and/or mechanical stimulators, such that the first portion of the leg is stimulated;
if the first stimulation is applied to the first portion, measuring, by the one or more measuring circuitries, a further electrical characteristic indicative of the physiological condition in the first portion of the leg via the first subset of skin electrodes;
determining, by evaluating the measured further electrical characteristic, if the first stimulation of the leg is to be terminated;
if it is determined that the first stimulation is to be terminated, configuring the first subset of electrical and/or mechanical stimulators such that the applied first stimulation of the leg is terminated;
measuring, by the one or more measuring circuitries, an electrical characteristic indicative of the physiological condition in a second portion of the leg via a second subset of skin electrodes comprised in the plurality of skin electrodes, wherein the second portion of the leg is different than the first portion of the leg, and wherein the second subset of skin electrodes is different than the first subset of skin electrodes;
determining, by evaluating the second measured electrical characteristic from the second portion of the leg, if the second portion of the leg is to be stimulated; and
if it is determined that the second portion is to be stimulated, applying a second stimulation via a second subset of electrical and/or mechanical stimulators, comprised in the plurality of electrical and/or mechanical stimulators, such that the second portion of the leg is stimulated, wherein the second subset of electrical and/or mechanical stimulators is different than the first subset of electrical and/or mechanical stimulators,
wherein measuring the electrical characteristic indicative of the physiological condition in the second portion of the leg occurs in response to the first stimulation being terminated and wherein each electrical and/or mechanical stimulator in the plurality of electrical and/or mechanical stimulators is connected to a controller by a respective single interconnection.

9. The stimulation system according to claim 8, wherein each of the first and second subsets of electrical and/or mechanical stimulators comprises an electrical stimulator, a mechanical stimulator, or both.

10. The stimulation system according to claim 8, wherein each of the first and second subsets of skin electrodes comprises at least one pair of skin electrodes.

11. The stimulation system according to claim 8, wherein the plurality of electrical and/or mechanical stimulators comprises electronic stimulators formed by one or more of the plurality of skin electrodes.

12. The stimulation system according to claim 8, further comprising an accelerometer or an inertial measurement unit arranged to be integrated in the garment and arranged to measure a movement of the leg, wherein the controller is arranged to further evaluate the measured movement for determining if the first and second portions of the leg are to be stimulated.

13. The stimulation system according to claim 8, wherein the plurality of skin electrodes are arranged to measure impedance.

14. The stimulation system according to claim 8, wherein the plurality of skin electrodes are arranged to measure an electrical muscle potential.

15. The stimulation system according to claim 14, wherein each of the first and second subsets of skin electrodes further comprise a reference skin electrode.

16. A garment adapted to be worn about at least a part of a human leg, the garment comprising a stimulation system according to claim 8.

17. The garment according to claim 16, wherein the garment forms at least part of a stocking, tights, a sleeve, or a sock.

* * * * *